United States Patent [19]

Hayashi

[11] Patent Number: 4,771,181
[45] Date of Patent: Sep. 13, 1988

[54] METHOD FOR DETECTING DRIPPING DROPLET WITH REFRACTED AND REFLECTED LIGHT

[75] Inventor: Ken-ichi Hayashi, Kodaira, Japan

[73] Assignee: Doryokuro Kakunenryo Kaihatsu Jigyodan, Tokyo, Japan

[21] Appl. No.: 73,696

[22] Filed: Jul. 14, 1987

[30] Foreign Application Priority Data

Jul. 14, 1986 [JP] Japan ................... 61-165111

[51] Int. Cl.⁴ ...................... G01N 21/86; G01N 15/02
[52] U.S. Cl. ...................................... 250/560; 356/336
[58] Field of Search ............... 356/343, 336, 338, 379, 356/384–387; 250/560, 573, 574; 73/865.5

[56] References Cited

U.S. PATENT DOCUMENTS

| | | | |
|---|---|---|---|
| 3,807,870 | 4/1974 | Kalman | 250/560 |
| 4,595,291 | 6/1986 | Tatsuno | 356/336 |
| 4,676,638 | 6/1987 | Yasuda | 250/573 |
| 4,701,051 | 10/1987 | Buchhave et al. | 356/336 |
| 4,709,156 | 11/1987 | Murphy et al. | 250/560 |

OTHER PUBLICATIONS

Bachalo, "Method for Measuring the Size and Velocity of Spheres by Dual Beam Light Scatter Interferometry", Applied Optics vol. 19, No. 3, 2/80, pp. 363–369.

Primary Examiner—David C. Nelms
Assistant Examiner—Michael Messinger
Attorney, Agent, or Firm—Wenderoth, Lind & Ponack

[57] ABSTRACT

A method for detecting a dripping transparent droplet which can preferably be applied to remotely and successively detect the leak of a liquid in a place inaccessible by a person. The method comprises subjecting parallel rays of light to enter the dripping droplet to generate light scattered from the droplet at a predetermined scattering angle, the scattered light being composed of light reflected by the surface of the droplet and light transmitted and refracted in the droplet and then emitted from the surface thereof. The scattered light is imaged on a one-dimensional photosensor by an optical imaging system to form in the image two luminescent spots resulting from the reflected light and the transmitted-refracted light and a diameter of the droplet is determined from a distance between two luminescent spots and a magnification of the optical imaging system.

5 Claims, 3 Drawing Sheets

METHOD FOR DETECTING DRIPPING DROPLET WITH REFRACTED AND REFLECTED LIGHT

BACKGROUND OF THE INVENTION

The present invention relates generally to a method for remotely measuring the size of a dripping droplet, and specifically it relates to a method for detecting the dripping droplet which can preferably be applied to remotely and successively detect the leak of a liquid in a place inaccessible by a person, e.g. in a radiation environment, and to measure the leakage thereof accurately.

A prior art method has been known wherein a shadow of a dropping object formed when light from a light source is intercepted by the object is detected to remotely measure the size of the object.

One example of such a prior art method will be described in detail with reference to FIG. 8. In the state in which light emitted from a light source 1 is received constantly by a one-dimensional photosensor 3 such as a CCD (Charged Coupled Device of semiconductor) line sensor, the light is intercepted when a droppoing object 2, that is an object of detection, drops transversely between the light sensor 1 and the one-dimensional photosensor 3. FIG. 9 is a graph of the intensity of the light at that time which is detected as an electric signal by the one-dimensional photosensor 3, and the size of the object 2 can be measured from the width of a dark portion.

When the above-described prior art method is applied to detect a transparent object such as a dripping water droplet, however, a luminescent spot appears also in the central portion of an image due to the light transmitted through the transparent droplet as shown in FIG. 10, and consequently an electric signal is divided into two. As a result, there occurs a possibility that one object is detected as two. Moreover, since the light from the light source 1 is not parallel, it turns round along the object and reaches the one-dimensional photosensor 3, thus making the boundary of the dark portion (the shadow of the object) indistinct. In addition, the one-dimensional photosensor 3 receives the light from the light source 1 constantly and detects the shadow formed by the object, and therefore it detects the dark portion in bright light. Accordingly, a state that the electric signals are delivered constantly from the photosensor 3 constitutes the background, and this results in a fault of increased background noise.

SUMMARY OF THE INVENTION

An object of the present invention is to provide an improved method for remotely and successively measuring the size of a transparent object such as a dripping water droplet.

A further object of the present invention is to provide a method for detecting a dripping droplet which can remarkably reduce the background noise generated from a photosensor to thereby accomplish the accurate detection.

According to the present invention, a source of parallel light is employed, and parallel rays of light emitted from this source enter a dripping transparent droplet. The incident light is scattered by the droplet. The scattered light is composed of the light reflected by the surface of the droplet and the transmitted-refracted light which is transmitted and refracted in the droplet and then emitted from the surface thereof. Thus, when this droplet is observed with an angle (scattering angle), two luminescent spots formed by the reflected light and the transmitted-refracted light are seen on the droplet. In the present invention, the reflected and transmitted-refracted lights from the droplets are imaged on a one-dimensional photosensor by an optical imaging system, a distance between the two luminescent spots formed in the image by the reflected light and the transmitted-refracted light is measured, and the diameter of the droplet is determined from the thus measured distance and the magnification of the optical imaging system.

In one embodiment of the present invention, the parallel rays of light emitted from the source are formed in the shape of a slit and then subjected to enter the droplet. In another embodiment, the scattered light from the droplet may be imaged on the one-dimensional photosensor through a beam slit provided before the photosensor.

Further, the scattered light from the droplet may be imaged on the one-dimensional photosensor directly by the optical imaging system, or may be imaged on the photosensor by the optical imaging system after the scattered light is reflected by a mirror.

These and other objects and novel features of the present invention will become apparent from the following description when taken in conjunction with the accompanying drawings.

PREFERRED EMBODIMENTS OF THE INVENTION

Figure 4:
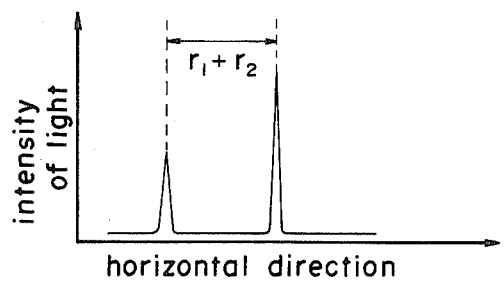
FIG. 4 is a graph of electric signals obtained from the image of FIG. 3 by a one-dimensional photosensor.

Hereinafter, the present invention will be described in further detail with reference to the preferred embodiments thereof shown in the accompanying drawings. FIGS. 1 to 5 illustrate the principal of the method of the present invention. When slit-shaped parallel rays of light emitted from a source 11 of parallel light in FIG. 1 enter, in one plane, a transparent dripping droplet 12 which is an object of detection, part of the incident light is reflected by the surface of the droplet to be scattered as reflected light, while part thereof is transmitted through the droplet, refracted therein and then emitted from the surface thereof tp be scattered as transmitted-refracted light. This is because the shape of the dripping droplet can be approximate to a true sphere. When the reflected light and the transmitted-refracted light are observed in the same plane as that of the parallel light and from the direction turned at an angle $\theta$ (scattering angle) with respect to the direction of advance of the parallel light, two luminescent spots, i.e. a luminescent spot A formed by the reflected light and a luminescent spot B formed by the transmitted-refracted light, can be seen in the droplet 12 as shown in FIG. 2. According to the present invention, instead of observing the luminescent spots in the actual droplet, rays of light propagated in the direction of the scattering angle are imaged on a one-dimensional photosensor 13 (FIG. 3) through an optical imaging system 14 such as a lens, and two luminescent spots a and b in the image thus formed can be obtained as electric signals from the one-dimensional photosensor 13 (FIG. 4).

Figure 5:
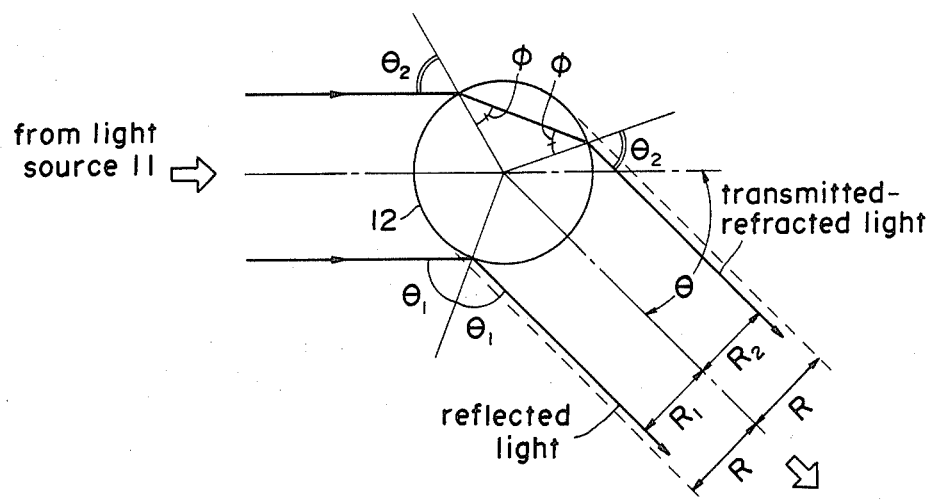
FIG. 5 is an illustration of conditions in terms of geometrical optics when parallel rays of light are scattered by the droplet.

FIG. 5 shows concretely the angle at which the incident light is scattered by the droplet, as well as the way of propagation of the incident light in the direction of the one-dimensional photosensor 13. Based on this figure, there will be explained conditions in terms of geometrical optics met by the rays of light out of the parallel ones which are scattered in the direction of the angle $\theta$. First, as to the reflected light out of the scattered light, angles formed by the incident light and the reflected light with respect to a perpendicular line drawn to the surface of the droplet 12 are equal, and when these angles are denoted by $\theta_1$, the relationship thereof with the scattering angle is expressed by the following equation (1):

$$\theta_1 = (\pi - \theta)/2 \quad (1)$$

As to the transmitted-refracted light, on the other hand, the equation (2) can be established when angles formed by the incident light and the refracted light with respect to perpendicular lines drawn to the surface of the droplet 12 are denoted by $\theta_2$ and $\phi$, respectively:

$$\theta_2 = (\theta + 2\phi)/2 \quad (2)$$

If the refractive index of the droplet is denoted by n, the following equation (3) is established according to the law of refraction:

$$\sin \theta_2 / \sin \phi = n \quad (3)$$

When this droplet 12 is observed from the direction of the one-dimensional sensor 13, two luminescent spots A and B corresponding to the angle $\theta_1$ meeting the equation (1) and and angle $\theta_2$ meeting the equations (2) and (3), respectively, are to be seen on the droplet (FIG. 2), and an image of the droplet 12 is to be formed with a magnification m on the one-dimensional photosensor 13 (FIG. 3) by using the optical imaging system 14. In fact, the diameter of the droplet itself can not be known directly from the signals obtained from the one-dimensional photosensor 13 (FIG. 4), but only a distance $r_1 + r_2$ between the two luminescent spots a and b on the one-dimensional photosensor can be known.

By the way, other rays of light out of the parallel ones are also reflected by the surface of the droplet or transmitted and refracted therein. However, these rays are scattered in directions other than that of the scattering angle $\theta$ since they do not meet the above-stated conditions in terms of geometrical optics, and therefore they do not reach the one-dimensional photosensor 13.

The actual diameter of the droplet is determined in the following manner by using the above-described relationships. When the actual radius of the droplet 12 is denoted by R, distances from the center of the droplet to the reflected light and the transmitted-refracted light viewed from the direction of $\theta$ by $R_1$ and $R_2$, respectively (FIGS. 2 and 5), and the radius and distances in the image on the one-dimensional photosensor 13 corresponding to the aforesaid radius and distances by r, $r_1$ and $r_2$, respectively, the following relationships are obtained:

$$mR = r;\ mR_1 = r_1;\ mR_2 = r_2 \quad (4)$$

Moreover, the relationships between $r_1$ and r and between $r_2$ and r are respectively expressed as follows:

$$r_1 = r \sin \theta_1;\ r_2 = r \sin \theta_2 \quad (5)$$

Thus, the following equation (6) is obtained:

$$r = \frac{r_1 + r_2}{\sin \theta_1 + \sin \theta_2} \quad (6)$$

When $\theta_1$ and $\theta_2$ with respect to the scattering angle $\theta$ are determined beforehand by the equations (1) and (2), the value r can be determined from the equation (6), and the actual radius R of the droplet can be calculated by the following equation (7) according to the first equation of the expression (4).

$$R = \frac{1}{m} \cdot \frac{r_1 + r_2}{\sin \theta_1 + \sin \theta_2} \quad (7)$$

The volume of the droplet that can be regarded as a true sphere is calculated from the radius of the droplet thus determined, and the quantity of dripping droplets can be found by multiplying said volume by the number of the dripping droplets.

Figure 1:
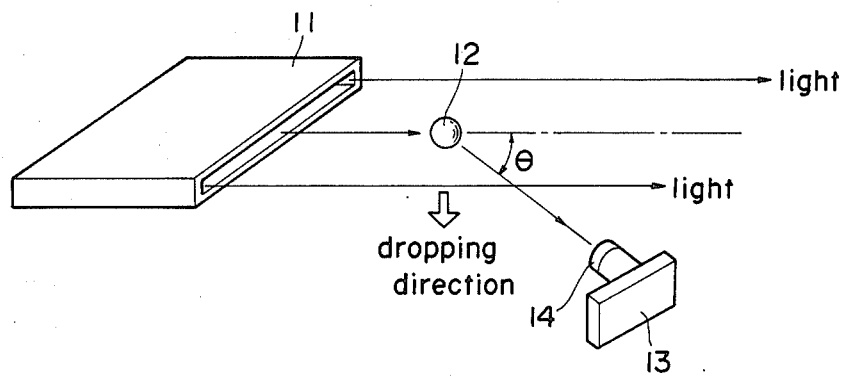
FIG. 1 is an illustration of a basic constitution of an apparatus for practicing a method of the present invention.
Figure 2:
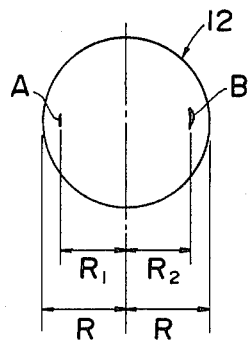
FIG. 2 is an illustration of an actual droplet and two luminescent spots therein.
Figure 3:
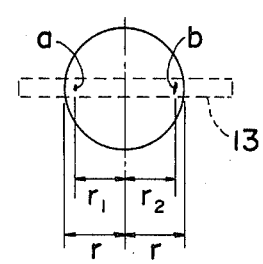
FIG. 3 is an illustration of an image of the droplet and two luminescent spots obtained by an optical imaging system.
Figure 6:
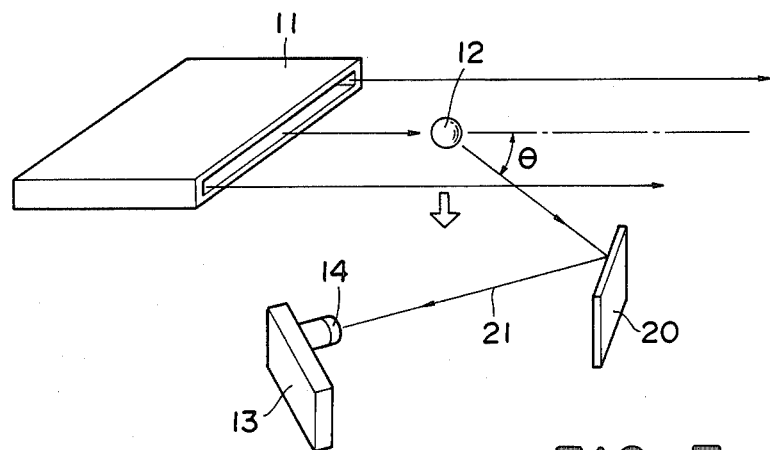
FIG. 6 is an illustration of another embodiment of an apparatus wherein the scattered light from the droplet is reflected by a mirror.

In the embodiment shown in FIG. 1, the one-dimensional photosensor 13 is installed at a position at which the scattered light from the droplet can directly be received. However, the constitution as shown in FIG. 6 may be employed in which the scattered light from the droplet 12 is once reflected by a mirror 20 and this scattered light 21 reflected by the mirror is received by the one-dimensional photosensor 13. According to this constitution as shown in FIG. 6, the restriction on the position of installation of the one-dimensional photosensor can be reduced.

Figure 7:
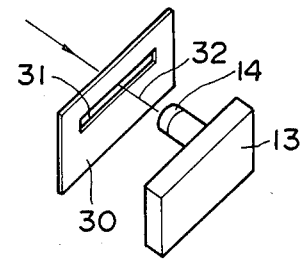
FIG. 7 is an illustration of other embodiment of an apparatus wherein a beam slit is provided before the one-dimensional photosensor.
Figure 8:
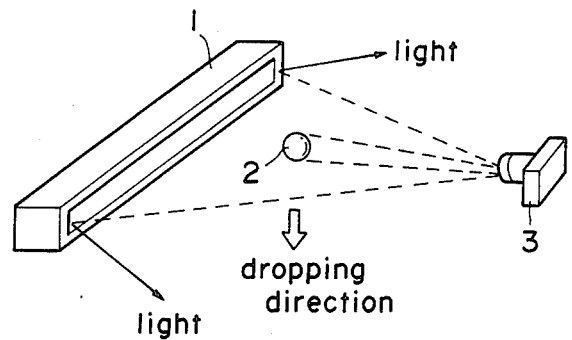
FIG. 8 is an illustration of a constitution of an apparatus for practicing a prior art method.
Figure 9:
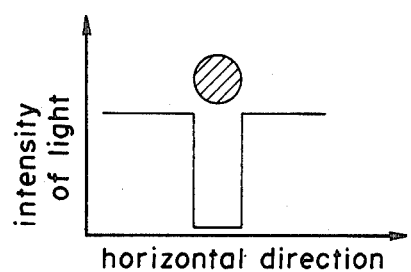
FIG. 9 is a graph of electric signals obtained by the one-dimensional photosensor when an opaque object is detected by the prior art method of FIG. 8.
Figure 10:
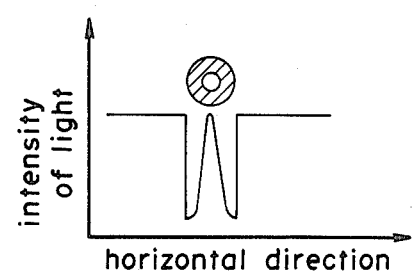
FIG. 10 is a graph of electric signals obtained by the one-dimensional photosensor when a transparent object is detected by the prior art method of FIG. 8.

Further, while the slit-shaped parallel rays are emitted from the light source in the embodiment shown in FIG. 1, parallel rays not in the shape of a slit may be used. In this case, a slit plate 30 having a beam slit 31 as shown in FIG. 7 is provided before the one-dimensional photosensor 13 so that only slit-shaped scattered light 32 transmitted through the beam slit 31 enteres the photosensor 13. When the scattered light entering the one-dimensional photosensor 13 is slit-shaped, noise incidental to detection by the one-dimensional photosensor can be reduced and consequently a sharp output waveform can be obtained, as compared with the case in which the slit-shaped light is not used.

As can be understood from the foregoing, according to the present invention, the size of the transparent dripping droplet can be measured remotely, succesively and accurately, by subjecting parallel rays of light to enter a transparent object such as a dripping droplet to scatter reflected light and transmitted-refracted light from the droplet, imaging the reflected light and the transmitted-refracted light on a one-dimensional photosensor, and detecting the image resulted from these reflected light and the transmitted-refracted light. Since the number of the dripping droplets can be measured simultaneously, the quantity of the dripping droplets can be determined from the size and the number of the droplets.

Moreover, since only the light scattered from the droplet at a predetermined scattering angle needs to be detected by the one-dimensional photosensor in this invention, the photosensor can be installed at a position where the light from the light source does not enter the sensor directly. Therefore, electric signals are outputted from the photosensor only when the scattered light from the droplet is detected, and this produces advantages that background noise can be made remarkably smaller than the one produced in a method such as of the prior art described previously wherein a dark portion is detected in bright light, and that the quantity of light can be detected easily and accurately as a result.

While preferred embodiments of the invention have been shown and described, it will be apparent to those skilled in the art that changes and modifications can be made in these embodiments without departing from the principles and spirit of the invention, the scope of which is defined in the appended claims.

What is claimed:

1. A method for detecting a dripping transparent droplet comprising: subjecting parallel rays of light to enter said dripping droplet to generate light scattered from said droplet at a predetermined scattering angle, said scattered light being composed of light reflected by the surface of said droplet and light transmitted and refracted in said droplet and then emitted from the surface thereof; imaging said scattered light on a one-dimensional photosensor by an optical imaging system to form in said image two luminescent spots resulting from said reflected light and said transmitted-refracted light; and determining a diameter of said droplet from a distance between said two luminescent spots and a magnification of said optical imaging system.

2. The method according to claim 1, wherein said parallel rays of light are formed in the shape of a slit and then subjected to enter said droplet.

3. The method according to claim 1, wherein said scattered light from said droplet is imaged on said one-dimensional photosensor through a beam slit provided before said photosensor.

4. The method according to claim 1, wherein said scattered light from said droplet is imaged on said one-dimensional photosensor directly by said optical imaging system.

5. The method according to claim 1, wherein said scattered light from said droplet is imaged on said one-dimensional photosensor by said optical imaging system after said scattered light is reflected by a mirror.

* * * * *